United States Patent [19]

Blass

[11] Patent Number: 4,996,056

[45] Date of Patent: Feb. 26, 1991

[54] DENTAL FLOSS AND TAPE

[75] Inventor: Jacob M. Blass, London, England

[73] Assignee: Westone Products Limited, London, England

[21] Appl. No.: 393,370

[22] Filed: Aug. 14, 1989

[30] Foreign Application Priority Data

Aug. 22, 1988 [GB] United Kingdom ................. 8819873

[51] Int. Cl.$^5$ .............................................. A61F 13/00
[52] U.S. Cl. .................................... 424/443; 424/434; 132/321
[58] Field of Search ................. 132/321; 424/434, 443

[56] References Cited

U.S. PATENT DOCUMENTS

| 3,838,702 | 10/1974 | Standish et al. | 132/321 |
| 3,930,059 | 12/1975 | Wells | 132/321 |
| 3,943,949 | 3/1976 | Ashton et al. | 132/321 |
| 4,029,113 | 6/1977 | Guyton | 132/321 |
| 4,836,226 | 6/1989 | Wolak | 132/321 |

FOREIGN PATENT DOCUMENTS 136727 10/1985 European Pat. Off. .
380032 8/1975 United Kingdom .

Primary Examiner—Merrell C. Cashion, Jr.
Assistant Examiner—Leon R. Horne
Attorney, Agent, or Firm—Larson and Taylor

[57] ABSTRACT

Fluorocarbon polymer powder particles, e.g. particulate PTFE, are included, as a solid lubricant, in the binder applied to dental floss or tape.

10 Claims, No Drawings

DENTAL FLOSS AND TAPE

This invention relates to dental floss and tape.

Dental floss and tape are well known products used for the cleaning of interdental gaps or as an underbridge dental cleaner. Floss and tape are generally similar but the tape has a flat cross sectional shape, while floss has a round cross sectional shape. Typically, floss or tape consists of a yarn of a large number of fine filaments, for example, of nylon or polyester, together with a binder which holds the filaments together in the yarn. The most common form of binder is wax, but non-wax coatings are also known, for example, polyvinyl acetate.

When wax is used as a binder, it has the advantage that it acts as a lubricant, making it easier for the user to pass the floss or tape between the teeth. Nevertheless, where the interdental gap is narrow, some users still find it difficult to pull the floss or tape between the teeth.

GB 1380032 discloses a packing material and a yarn which contains aromatic polyamide filaments and polytetrafluoroethylene filaments. The yarn may additionally be coated with finely divided polytetrafluoroethylene particles and may also be coated as well with polyorganosiloxane. The yarn is braided to form the packing material. PTFE is used in packaging materials because of its ability to withstand high temperatures and its chemical inertness.

EP 0136727 also discloses a further packing material and yarn which is coated in polyfluorocarbon, preferably mixed with graphite. The yarn is an aromatic polyamide, contains 1000 to 20000 filaments and has a density of 150 to 3000 tex.

According to the present invention there is provided dental floss or tape having a binder for the filaments thereof, wherein the binder contains solid lubricant in the form of fluorocarbon polymer powder particles. The effect of the solid lubricant is to reduce the coefficient of friction of the floss or tape with the teeth, thereby rendering it easier to pull the floss or tape through the interdental gap.

Any suitable solid lubricant of the fluorocarbon polymer type can be used, the most commonly available being PTFE (polytetrafluoroethylene). Other fluorocarbon polymers are polymers or copolymers of chlorotrifluoroethylene, fluorinated ethylene-propylene polyvinylidene fluoride, hexafluoropropylene, tetrafluoroethylene etc. Preferred are perfluoropolymers. The average particle size of the solid lubricant is preferably in the range 1 to 50 $\mu$m, or more preferably 5 to 30 $\mu$m. The content of the solid lubricant in the binder may be up to 80% by weight, but is preferably in the range 0.5% to 60%, or more preferably 5% to 40%. The most preferable weight range is 10 to 30%.

The invention is applicable both where a wax binder is used and where a non-wax binder is used. In the case of a wax binder, typically the content of the wax in the floss or tape is in the range 10 to 30 weight %, more preferably 15 to 23 weight %. In the case of a non-wax coating, such as polyvinyl acetate, the binder content in the floss or tape is somewhat lower, typically 5 to 15%.

Suitable materials for the filaments of the floss or tape are nylon, polyester and polypropylene, among many synthetic plastics materials. Generally speaking these materials are not absorbent. Typically dimensional ranges for floss and tape are 300 to 2000 dtex. Generally, floss has 30 to 120 turns per meter.

One specific embodiment of the invention is given by way of example. It is not limiting.

A continuous multifilament yarn of nylon (940 dtex ICI high-tenacity yarn, of 150 filaments, twisted 90 turns per meter) was passed through a bath of warm wax containing 20% of fine PTFE powder (ICI Fluon L169 of average particle size, as measured by Coulter Counter method, of 9.7 $\mu$m, 90% of the particles being below 20 $\mu$m). The take-up of wax including PTFE from the bath by the yarn was such that in the product 18% of the floss weight is wax plus PTFE. After passing through the bath, the yarn is passed between heated rollers which control the level of binder by pressure. Passage between the rollers forces the binder between the individual filaments.

In tests, this dental floss was found to be easier to pull through the interdental gaps than the identical floss without the PTFE powder, particularly where there are tight contact points. The reduction in friction is advantageous in that less binder is left on the teeth.

In consumer tests, a consumer preference was expressed for floss having PTFE in the binder. This was also true of double blind tests. Inclusion of PTFE powder has the added advantage of enhancing the appearance of the product by making it whiter. PTFE powder is white and acts as an "optical brightener". A "sticky feeling" occurring during or after flossing which is often caused by the wax in the binder, is removed by use of PTFE in the binder. The PTFE imparts a "dry" feel to floss and tape.

I claim:

1. A dental floss or tape comprising a multi-filament yarn and a binder between the individual filaments holding the filaments together in the yarn, and fluorocarbon polymer powder particles in said binder, said powder particles being present in an amount of up to 80% by weight based on the weight of the binder and having an average particle size in the range of 1 to 50 $\mu$m.

2. A dental floss or tape according to claim 1 wherein the fluorocarbon polymer comprises a polymer or copolymer of chlorotrifluoroethylene, fluorinated ethylene-propylene, polyvinylidene fluoride, hexafluoropropylene or tetrafluoroethylene.

3. A dental floss or tape according to claim 1 wherein the fluorocarbon polymer comprises polytetrafluoroethylene (PTFE).

4. A dental floss or tape according to claim 1 wherein the binder contains 0.5 to 60% by weight solid lubricant.

5. A dental floss or tape according to claim 1 wherein the average particle size is in the range 5 to 30 $\mu$m.

6. A dental floss or tape according to claim 1 wherein the binder comprises wax.

7. A dental floss or tape according to claim 6 wherein the content of wax in the floss or tape is in the range 10 to 30 weight %.

8. A dental floss or tape according to claim 1 wherein the binder comprises a non-wax binder and the non-wax binder content of the floss or tape is 2 to 15 weight %.

9. A dental floss or tape according to claim 7 wherein the wax binder contains from 0.5 to 60% by weight, based on the weight of wax binder, of said solid lubricant.

10. A dental floss or tape according to claim 8 wherein the wax binder contains from 0.5 to 60% by weight, based on the weight of wax binder, of said solid lubricant.

* * * * *